US00PP31630P2

(12) United States Plant Patent
Hansen

(10) Patent No.: US PP31,630 P2
(45) Date of Patent: Mar. 31, 2020

(54) **X *MANGAVE* PLANT NAMED 'PAINTED DESERT'**

(50) Latin Name: ***Agave* times x *Mangave* hybrid**
Varietal Denomination: Painted Desert

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 16/501,796

(22) Filed: Jun. 7, 2019

(51) Int. Cl.
*A01H 5/00* (2018.01)
*A01H 6/12* (2018.01)

(52) U.S. Cl.
USPC ..... Plt./373
CPC ..... *A01H 6/12* (2018.05)

(58) Field of Classification Search
USPC ..... Plt./373
CPC ..... A01H 5/00
See application file for complete search history.

*Primary Examiner* — Kent L Bell

(57) ABSTRACT

A new and unique x *Mangave* plant named 'Painted Desert' characterized by compact habit and lanceolate foliage with chartreuse green color with darker margins in lower ultraviolet light exposure and in high ultraviolet light exposure developing reddish mottling with glaucous covering speckling and blushing concentrated in the basal portions.

2 Drawing Sheets

Botanical classification: *Agave* times x *Mangave* hybrid. Variety denomination: 'Painted Desert'.

STATEMENT REGARDING PRIOR DISCLOSURES UNDER 37 CFR 1.77(B)(6)

The first non-enabling disclosure of the claimed plant, in the form of a private sale, was made by Walters Gardens, Inc. on Jul. 23, 2018 to Plant Delights Nursery, Inc. Plants for this sale were obtained from the inventor. Since then, on Feb. 14, 2019, the plant was first advertised on a website managed by Walters Gardens, Inc. No plants of x *Mangave* 'Painted Desert' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to the new and distinct x *Mangave* plant, x *Mangave* 'Painted Desert' that was hybridized by the inventor at a wholesale perennial nursery in Zeeland, Mich., USA as a cross between a proprietary unnamed selection of *Agave nizandensis* (not patented) as the female or seed parent times and x *Mangave* 'Bloodspot' (not patented) as the male or pollen parent. The cross was performed Jul. 10, 2014 and seeds were harvested and sown later the following autumn. Through trials at the same nursery the plant was referred to by the code 14-171-8. The new plant has been successfully asexually propagated by sterile shoot-tip tissue culture and by basal offsets at the same nursery in Zeeland, Mich. The asexual propagation by tissue culture and basal offsets has been found to produce stable and identical plants that maintain all the unique characteristics of the original plant.

BRIEF SUMMARY OF THE INVENTION

X *Mangave* 'Painted Desert' differs from its parents as well as all other *Manfreda, Agave* and x *Mangave* known to the applicant. The female parent has a flatter habit with fewer leaves per plant that are shorter and wider, has small marginal teeth, moderately channeled or concavo-convex with a lighter chartreuse along midrib, but the leaves do not have reddish spots or reddish pigmentation. The male parent is more upright in habit with greater number of leaves per plant, with foliage that is shorter, more glaucous, thicker (adaxial to abaxial), dark brown around the marginal teeth and larger terminal spines and fewer, less-overlapping, mahogany spots.

The most similar known X *Mangave* cultivar known to the inventor are: 'Blazing Saddles' U.S. Plant Pat. No. 31,274, 'Mission to Mars' U.S. Plant Pat. No. 29,393, 'Red Wing' U.S. Plant patent application Ser. No. 16/350,922, 'Thunderbird' U.S. Plant Pat. No. 31,248, 'Racing Stripes' U.S. Plant Pat. No. 31,251 and copending 'Shadow Waltz' U.S. Plant patent application Ser. No. 16/501,795.

'Blazing Saddles' has broader, more lustrous, less glaucous leaves with more reddish spotting in high light intensity. 'Mission to Mars' has much larger, broader foliage, larger marginal teeth, larger habit, less glaucous and the foliage is more solid red in high ultraviolet light. 'Red Wing' has more leaves per plant that are broader and the reddish coloration of cherry-red is more intense with more coverage of the leaf. 'Thunderbird' is more compact in habit, the leaves are shorter, thicker and more fibrous than the new plant. Both 'Red Wing' and 'Thunderbird' are predominantly reddish purple in foliage and lack the lighter chartreuse along the midrib. 'Racing Stripes' has wider leaves and more upright arching habit, more pronounced marginal teeth and the foliage has the lighter chartreuse along the midrib without any reddish purple spotting or mottling. 'Shadow Waltz' has more flexible marginal teeth and lacks the semi-flexible mucro at the leaf apex. 'Shadow Waltz' has the lighter chartreuse along the midrib and lacks the reddish purple spotting or mottling.

The new plant, 'Painted Desert', is unique from all of these variegated *Agave*, x *Mangave* and *Manfreda* known to the inventor by the following combined traits:

1. Compact habit with about 60 leaves;
2. Foliage lanceolate with small semi-flexible marginal teeth and semi-flexible sharp apex;
3. Foliage has chartreuse center and darker green margin and with high ultraviolet light develops reddish speckling concentrated proximally on leaves with glaucous covering on top and bottom;
4. Moderate growth rate;

BRIEF DESCRIPTION OF THE DRAWINGS

The photograph of the new plant demonstrates the overall appearance of the new plant including the unique traits as a three-year-old plant grown with supplemental water and fertilizer as needed. The colors are as accurate as reasonably possible with color reproductions. Ambient light spectrum, temperature, source and direction may cause the appearance of minor variation in color.

DETAILED BOTANICAL DESCRIPTION

Figure 1:
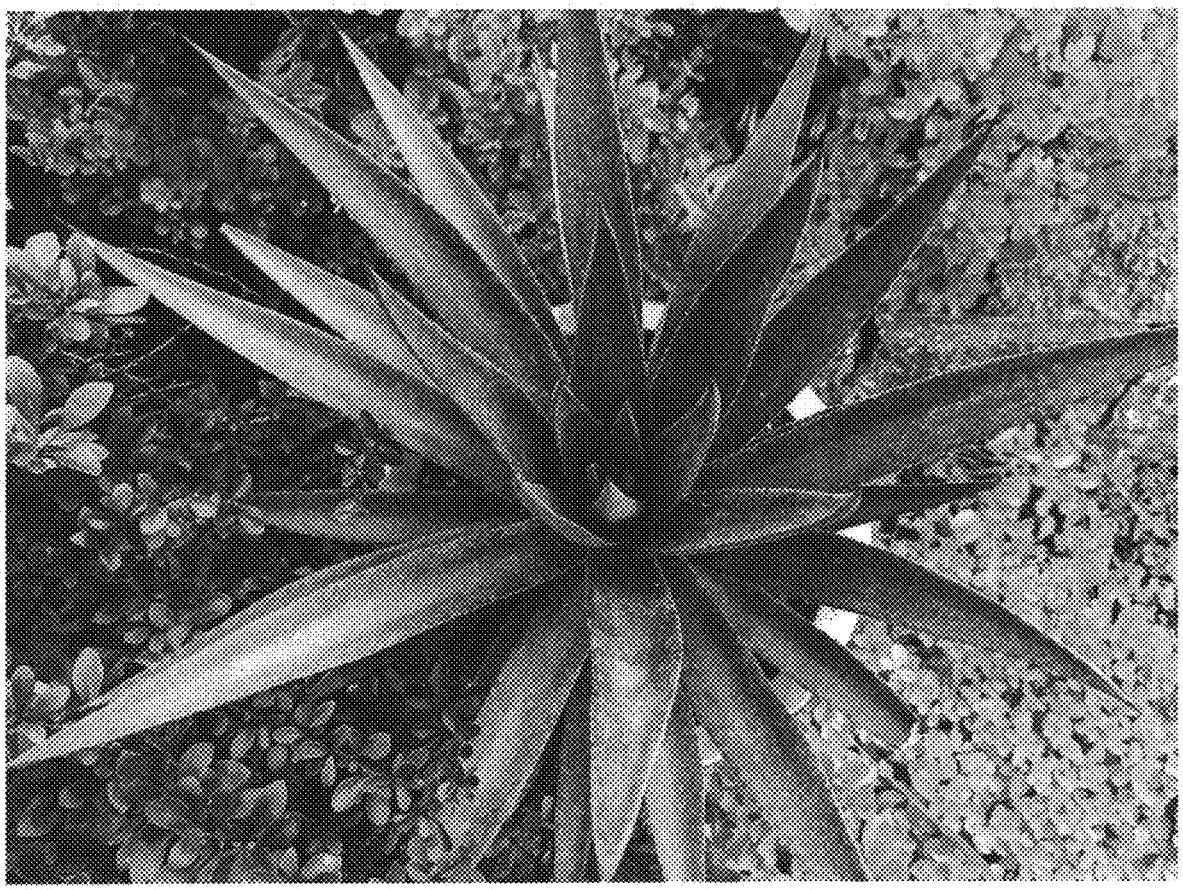
FIG. 1 shows the new plant in a container in a greenhouse and followed up with growing in full sun in an outdoor trial garden.
Figure 2:
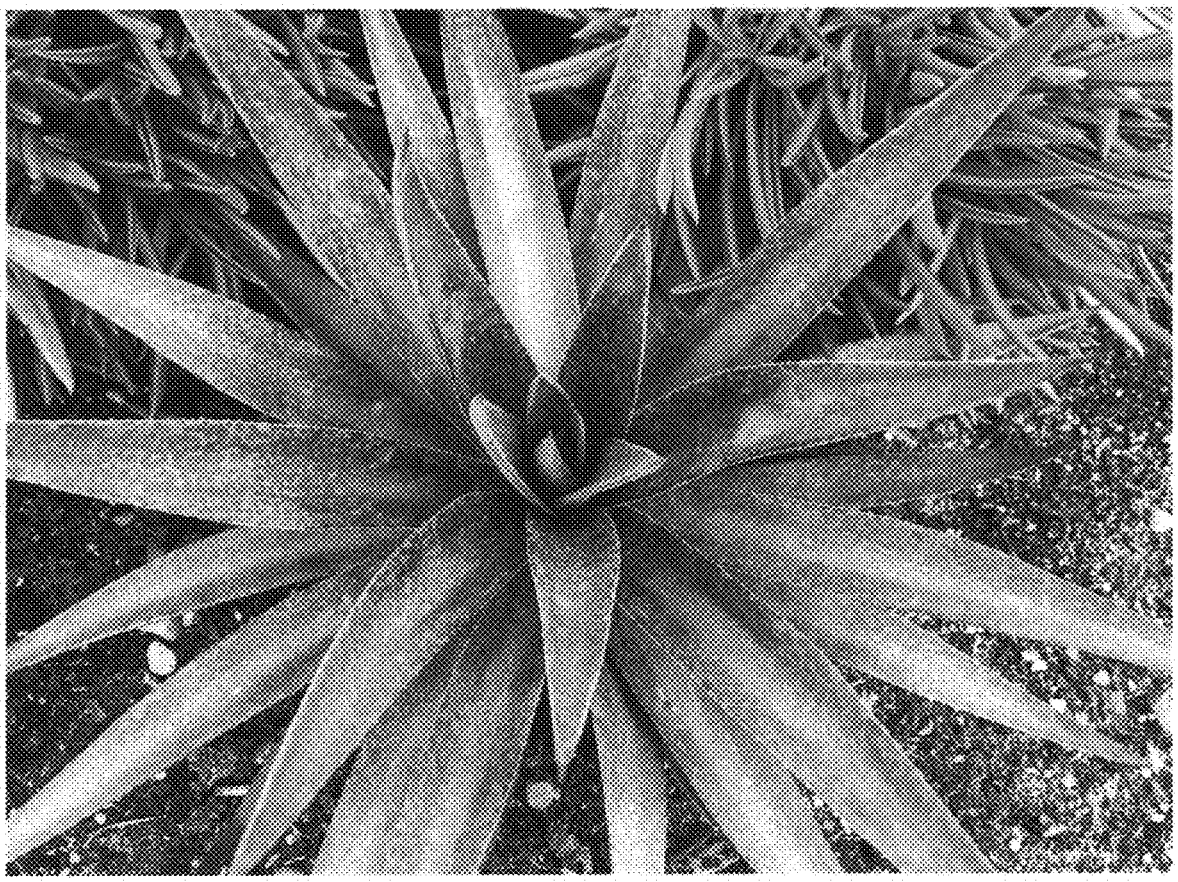
FIG. 2 shows the new plant grown in a full sun outdoor trial garden.

The following descriptions and color references are based on the 2015 edition of The Royal Horticultural Society Colour Chart except where common dictionary terms are used. The new plant, x *Mangave* 'Painted Desert', has not been observed under all possible environments. The phenotype may vary slightly with different environmental conditions, such as temperature, light, fertility, moisture and maturity levels, but without any change in the genotype. The following observations and size descriptions are of two and three-year old plants in a commercial wholesale greenhouse and in a full sun outdoor trial garden in Zeeland, Mich. with supplemental water and fertilizer as needed.

Botanical classification: *Agave* times x *Mangave* hybrid;

Variety denomination: 'Painted Desert';

Parentage: A proprietary unnamed selected form of *Agave nizandensis* as the female or seed parent and x *Mangave* 'Bloodspot' as the male or pollen parent;

Propagation: Core division and sterile plant tissue culture;

Time to initiate roots from tissue culture: About 21 days;

Growth rate: Moderate;

Crop time: About 16 to 18 weeks to finish during lengthening spring days from an established 25 mm tissue culture plug to a 65 mm diameter container;

Rooting habit: Fleshy, lightly branching, with roots up to 15 cm long;

Root color: Nearest RHS 158C;

Plant shape and habit: Succulent herbaceous perennial with basal rosettes of up to about 60 fleshy leaves radially emerging and arching from central rhizome, producing a symmetrical rounded mound;

Plant size: Foliage height about 30.0 cm tall from soil line to the top of the leaves and to about 51.0 cm wide at the widest point at soil line;

Foliage description: Lanceolate; simple; fleshy; fibrous; glabrous; margins finely dentate with semi-flexible teeth; apex acute with semi-flexible mucro; base truncate, sessile, clasping;

Leaf size: To about 32.0 cm long, about 36.0 mm wide at base and 5.0 mm thick near base, average about 27.5 cm long, 32.0 mm wide and 5.0 mm thick; usually bi-laterally symmetrical; glabrous and slightly glaucous above and below; abaxial and adaxial reddish spots of variable sizes from about 2.0 mm diameter to about 7.0 mm long and 4.0 mm across concentrated proximally; margin of variable width between 6.0 mm and 12.0 mm adaxial and 3.0 mm and 5.0 mm abaxial; teeth 1.0 mm long and 1.0 mm across at base about 1.8 mm apart; mucro about 6.0 mm long and 1.0 mm wide;

Foliage fragrance: None observed;

Leaf blade color:

*Adaxial* (*low ultraviolet exposure*).—Young and mature margin nearest RHS NN137B, center nearest RHS 146B.

*Abaxial* (*low ultraviolet exposure*).—Young and mature margin nearest RHS 137B, center nearest RHS 146B.

*Adaxial* (*high ultraviolet exposure*).—Young margin mottled with nearest RHS 137B and RHS 187B concentrated proximally with glaucous covering nearest RHS N187C; young center nearest RHS 146D maculate with spots of nearest RHS 187D with glaucous covering nearest RHS N187C; mature margin mottled with nearest RHS 137B and nearest RHS N186C; mature center nearest RHS 187D toward base and mottled with nearest RHS 186C and RHS 146C distally.

*Abaxial* (*high ultraviolet exposure*).—Young margin and center mottled with RHS 137C and RHS 186C concentrated at base and covered with glaucous bloom nearest RHS N187C; mature margin nearest RHS 137B maculate with spots of nearest RHS N186C concentrated proximally; mature center nearest RHS 144A maculate with spots of nearest RHS N186C.

*Teeth*.—Abaxial and adaxial nearest RHS 160C.

Mucro: Terminal spine; semi-flexible; straight; sharply pointed; about 6.0 mm long and 1.0 mm wide;

Mucro color: Nearest RHS 173A on young leaves, becoming nearest RHS 200B with maturity;

Petiole: Sessile;

Veins: Parallel; not distinct;

Flowering and fruiting have not yet been observed.

Disease resistance: X *Mangave* 'Painted Desert' has not been observed to be resistant to diseases common to other x *Mangave* beyond that which is normal for *Agave* or *Manfreda*. The plant is xeromorphic and survives well with minimal water once established. Hardiness at least from USDA zone 9 to 11. Full extent of winter hardiness has not been tested.

I claim:

1. A new and distinct cultivar of ornamental x *Mangave* plant named 'Painted Desert' as herein described and illustrated.

* * * * *